(12) United States Patent
Lee et al.

(10) Patent No.: US 7,291,638 B2
(45) Date of Patent: Nov. 6, 2007

(54) 3-AMIDO-1,2-BENZOISOXAZOLE DERIVATIVES, PROCESS FOR PREPARATION, AND USE THEREOF

(75) Inventors: Jin-Soo Lee, Yongin-si (KR); Seok-Hoon Ahn, Seoul (KR); Young-Goo Jin, Seoul (KR); Sang-Mi Jin, Yongin-si (KR); Sae-Kwang Ku, Suwon-si (KR); Jei-Man Rye, Anyang-si (KR); Yong-Ho Chung, Anyang-si (KR); Eun-Joo Kim, Taejon-si (KR); Sun-Ki Cho, Anyang-si (KR)

(73) Assignee: Dongwha Pharm. Ind. Co., Ltd., Seoul (KR)

( * ) Notice: Subject to any disclaimer, the term of this patent is extended or adjusted under 35 U.S.C. 154(b) by 676 days.

(21) Appl. No.: 10/493,702

(22) PCT Filed: Nov. 5, 2002

(86) PCT No.: PCT/KR02/02058

§ 371 (c)(1),
(2), (4) Date: Apr. 27, 2004

(87) PCT Pub. No.: WO03/040113

PCT Pub. Date: May 15, 2003

(65) Prior Publication Data

US 2005/0020650 A1    Jan. 27, 2005

(30) Foreign Application Priority Data

Nov. 6, 2001 (KR) .................. 10-2001-0069013

(51) Int. Cl.
*A61K 31/42* (2006.01)
*C07D 261/20* (2006.01)

(52) U.S. Cl. .............. 514/379; 548/240; 548/241; 514/378; 514/380

(58) Field of Classification Search ............... 548/240, 548/241; 514/318, 319, 380
See application file for complete search history.

(56) References Cited

U.S. PATENT DOCUMENTS 6,150,390 A * 11/2000 Suh et al. ............... 514/379

FOREIGN PATENT DOCUMENTS

| JP | 2-237956 | 9/1990 |
| WO | WO98/33779 | 8/1998 |

OTHER PUBLICATIONS

Franchi-Miller, C. et al., "The 5-lipoxygenase Inhibitor BWA4C Impairs Osteoclastic Resorption in a Synchronized Model of Bone Remodeling". Bone, vol. 17, No. 2, Aug. 1995, pp. 185-191.
Kuwabara, Kenji, et al., "Effects of the second-generation leukotriene $B_4$ receptor antagonist, LY293111Na, on leukocyte infiltration and collagen-induced arthritis in mice". European Journal of Pharmacology, vol. 402, 2000, pp. 275-285.
Suh, Hongsuk, et al., "3-Amino-1,2-benzisoxazoles: A New Family of Potent Inhibitors of LTB, Binding to the Human Neutrophils". Bioorganic & Medical Chemistry Letters, vol. 7, No. 4, 1997, pp. 389-392.

* cited by examiner

*Primary Examiner*—Golam M. M. Shameem
(74) *Attorney, Agent, or Firm*—The Nath Law Group; Gary M. Nath; Tanya E. Harkins

(57) ABSTRACT

The present invention relates to 3-amido-1,2-benzoisoxazole derivatives and their salts represented by formula 1, processes for preparation and usees thereof. More particularly, it relates to a method for improving its bioavailability introducing amino acid residue to the amine group of a 3-amido-1,2-benzoisoxazole. The compounds according to the present invention are used as an antagonist against Leukotriene-B-4 receptor, an inhibitor or therapeutics of osteoroposis, thus inhibiting osteolysis and stimulating osteogensis.

6 Claims, No Drawings

3-AMIDO-1,2-BENZOISOXAZOLE DERIVATIVES, PROCESS FOR PREPARATION, AND USE THEREOF

TECHNICAL FIELD

The present invention relates to 3-amido-1,2-benzoisoxazole derivatives and their salts represented by formula 1, processes for preparation and uses thereof. More particularly, it relates to a method for improving its bioavailability by introducing amino acid residue to the amine group of a 3-amido-1,2-benzoisoxazole.

[formula 1]

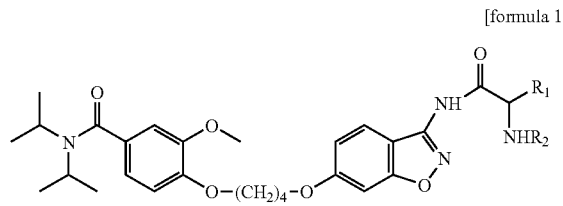

(wherein, $R_1$ is hydrogen, hydroxymethyl group, straight or branched alkyl group of $C_1$~$C_6$, benzyl group or 2-methylthioethyl group;

$R_2$ is hydrogen or —COCH(NH$_2$)R$_3$; and $R_3$ is hydrogen, hydroxymethyl group, straight or branched alkyl group of $C_1$~$C_6$, benzyl group or 2-methylthioethyl group.)

BACKGROUND ART

The present inventors synthesized 3-amido-1,2-benzoisoxazole derivatives represented by the following formula 2 while they synthesized compounds of various structures and verified their efficiency as antagonists against the Leukotriene-B-4 (hereinafter referred to as LTB-4) receptor and their osteogenesis stimulation effect in order to treat various diseases related to LTB-4. It has been found out that compounds of the following formula 2 have simultaneous efficiency in showing antagonism against the LTB-4 receptor and in stimulating osteogenesis (Korea Patent Application No. 1998-71076A; U.S. Pat. No. 6,150,390). However, they also have a disadvantage that they are inadequate to be used as a drug since the bioavailability is not so good.

[formula 2]

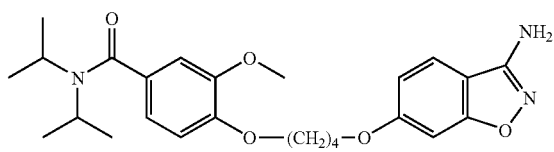

(wherein, n is an integer of 3 to 5.)

Hereupon, the present inventors synthesized novel 3-amido-1,2-benzoisoxazole derivatives represented by formula 1 of the present invention by introducing amino acid residue to the amine group of a 3-amido-1,2-benzoisoxazole in order to improve the bioavailability of compounds of the above formula 2. In addition, they completed this invention by finding out that compounds of the present invention not only showed efficiency as antagonists against LTB-4 receptor, inhibitors of osteolysis and stimulators of osteogenesis but also increased solubility in water and improved bioavailability by having high absorption ratio in vivo, and thus, improved their medical effect.

DISCLOSURE OF THE INVENTION

It is therefore an object of the present invention to provide 3-amido-1,2-benzoisoxazole derivatives or their pharmaceutically acceptable acidic additive salts represented by formula 1, improving bioavailability by introducing amino acid residue to amine group of a 3-amido-1,2-benzoisoxazole.

It is another object of the present invention to provide methods of preparing 3-amido-1,2-benzoisoxazole derivatives or their pharmaceutically acceptable acidic additive salts represented by formula 1.

It is still another object of the present invention to provide pharmaceutical compositions as antagonists against LTB-4 receptor, including 3-amido-1,2-benzoisoxazole derivatives or their pharmaceutically acceptable acidic additive salts represented by formula 1, as effective ingredients.

It is a further object to provide the pharmaceutical compositions as inhibitors or therapeutics of osteoporosis, including 3-amido-1,2-benzoisoxazole derivatives or their pharmaceutically acceptable acidic additive salts represented by formula 1, as effective ingredients.

BEST MODE OF CARRYING OUT THE INVENTION

The present invention provides 3-amido-1,2-benzoisoxazole derivatives represented by the following formula 1, improving the bioavailability by introducing amino acid residue to the amine group of the 3-amido-1,2-benzoisoxazole.

[formula 1]

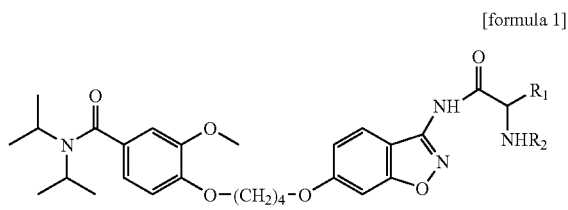

(wherein, $R_1$ is hydrogen, hydroxymethyl group, straight or branched alkyl group of $C_1$~$C_6$, benzyl group or 2-methylthioethyl group;

$R_2$ is hydrogen or —COCH(NH$_2$)R$_3$; and $R_3$ is hydrogen, hydroxymethyl group, straight or branched alkyl group of $C_1$~$C_6$, benzyl group or 2-methylthioethyl group.)

The present invention provides compounds represented by the followings, according to $R_1$ and $R_2$ of the formula 1.

I. $R_2$ is hydrogen, $R_1$ is hydrogen, hydroxymethyl group, straight or branched alkyl group of $C_1$~$C_6$, benzyl group or 2-methylthioethyl group, 1) N,N-diisopropyl-4-{4-[3-(2-amino-1-oxoethyl)aminobenzo[d]isoxazole-6-yl-oxy]butoxy}-3-methoxybenzamide (1a);

2) N,N-diisopropyl-4-{4-[3-(2-amino-1-oxopropyl)aminobenzo[d]isoxazole-6-yl-oxy]butoxy}-3-methoxybenzamide (1b);

3) N,N-diisopropyl-4-{4-[3-(2-amino-3-phenyl-1-oxopropyl)aminobenzo[d]isoxazole-6-yl-oxy]butoxy}-3-methoxybenzamide (1c);

4) N,N-diisopropyl-4-{4-[3-(2-amino-3-methyl-1-oxobutyl)aminobenzo[d]isoxazole-6-yl-oxy]butoxy}-3-methoxybenzamide (1d);

5) N,N-diisopropyl-4-{4-[3-(2-amino-4-thiomethyl-1-oxobutyl)aminobenzo[d]isoxazole-6-yl-oxy]butoxy}-3-methoxybenzamide (1e);

II. $R_2$ is —$COCH(NH_2)R_3$, $R_1$ is hydrogen and straight or branched alkyl group of $C_1$~$C_6$, preferably hydrogen (a starting material is the compound 1a), $R_3$ is hydrogen, hydroxymethyl group, straight or branched alkyl group of $C_1$~$C_6$, benzyl group or 2-methylthioethyl group, 6) N,N-diisopropyl-4-(4-{3-[2-(2-amino-1-oxoethyl)amino-1-oxoethyl]aminobenzo[d]isoxazole-6-yl-oxy}butoxy)-3-methoxybenzamide (1f);

7) N,N-diisopropyl-4-{4-{3-[2-(2-amino-1-oxopropyl)amino-1-oxoethyl]aminobenzo[d]isoxazole-6-yl-oxy}butoxy}-3-methoxybenzamide (1 g);

8) N,N-diisopropyl-4-{4-{3-[2-(2-amino-3-phenyl-1-oxopropyl)amino-1-oxoethyl]-aminobenzo[d]isoxazole-6-yl-oxy}butoxy}-3-methoxybenzamide (1 h);

9) N,N-diisopropyl-4-{4-{3-(2-(2-amino-3-methyl-1-oxobutyl)amino-1-oxoethyl)aminobenzo[d]isoxazole-6-yl-oxy}butoxy}-3-methoxybenzamide (1i);

10) N,N-diisopropyl-4-{4-{3-[2-(2-amino-4-thiomethyl-1-oxobutyl)amino-1-oxoethyl]aminobenzo[d]isoxazole-6-yl-oxy}butoxy}-3-methoxybenzamide (1j);

III. $R_2$ is —$COCH(NH_2)R_3$, $R_1$ is straight or branched alkyl group of $C_1$~$C_6$, preferably methyl group (a starting material is the compound 1b), $R_3$ is hydrogen, hydroxymethyl group, straight or branched alkyl group of $C_1$~$C_6$, benzyl group or 2-methylthioethyl group, 11) N,N-diisopropyl-4-{4-{3-[2-(2-amino-1-oxoethyl)amino-1-oxopropyl]aminobenzo[d]isoxazole-6-yl-oxy}butoxy}-3-methoxybenzamide (1k);

12) N,N-diisopropyl-4-{4-{3-[2-(2-amino-1-oxopropyl)amino-1-oxopropyl]aminobenzo[d]isoxazole-6-yl-oxy}butoxy}-3-methoxybenzamide (1l);

13) N,N-diisopropyl-4-{4-{3-[2-(2-amino-3-phenyl-1-oxopropyl)amino-1-oxopropyl]aminobenzo[d]isoxazole-6-yl-oxy}butoxy}-3-methoxybenzamide (1m);

14) N,N-diisopropyl-4-{4-{3-[2-(2-amino-3-methyl-1-oxobutyl)amino-1-oxopropyl]aminobenzo[d]isoxazole-6-yl-oxy}butoxy}-3-methoxybenzamide (1n);

15) N,N-diisopropyl-4-{4-{3-[2-(2-amino-4-thiomethyl-1-oxobutyl)amino-1-oxopropyl]aminobenzo[d]isoxazole-6-yl-oxy}butoxy}-3-methoxybenzamide (1o);

IV. $R_2$ is —$COCH(NH_2)R_3$, $R_1$ is benzyl group (a starting material is the compound 1c), $R_3$ is hydrogen, hydroxymethyl group, straight or branched alkyl group of $C_1$~$C_6$, benzyl group or 2-methylthioethyl group, 16) N,N-diisopropyl-4-{4-{3-[2-(2-amino-1-oxoethyl)amino-3-phenyl-1-oxopropyl]aminobenzo[d]isoxazole-6-yl-oxy}butoxy}-3-methoxybenzamide (1p);

17) N,N-diisopropyl-4-{4-{3-[2-(2-amino-1-oxopropyl)amino-3-phenyl-1-oxopropyl]aminobenzo[d]isoxazole-6-yl-oxy}butoxy}-3-methoxybenzamide (1q);

18) N,N-diisopropyl-4-{4-{3-[2-(2-amino-3-phenyl-1-oxopropyl)amino-3-phenyl-1-oxopropyl]aminobenzo[d]isoxazole-6-yl-oxy}butoxy}-3-methoxybenzamide (1r);

19) N,N-diisopropyl-4-{4-{3-[2-(2-amino-3-methyl-1-oxobutyl)amino-3-phenyl-1-oxopropyl]aminobenzo[d]isoxazole-6-yl-oxy}butoxy}-3-methoxybenzamide (1s);

20) N,N-diisopropyl-4-{4-{3-[2-(2-amino-4-thiomethyl-1-oxobutyl)amino-3-phenyl-1-oxopropyl]aminobenzo[d]isoxazole-6-yl-oxy}butoxy}-3-methoxybenzamide (1t);

V. $R_2$ is —$COCH(NH_2)R_3$, $R_1$ is straight or branched alkyl group of $C_1$~$C_6$, preferably isopropyl group (a starting material is the compound 1d)

$R_3$ is hydrogen, hydroxymethyl group, straight or branched alkyl group of $C_1$~$C_6$, benzyl group or 2-methylthioethyl group, 21) N,N-diisopropyl-4-{4-{3-[2-(2-amino-1-oxoethyl)amino-3-methyl-1-oxobutyl]aminobenzo[d]isoxazole-6-yl-oxy}butoxy}-3-methoxybenzamide (1u);

22) N,N-diisopropyl-4-{4-{3-[2-(2-amino-1-oxopropyl)amino-3-methyl-1-oxobutyl]aminobenzo[d)isoxazole-6-yl-oxy}butoxy}-3-methoxybenzamide (1v);

23) N,N-diisopropyl-4-{4-{3-[2-(2-amino-3-phenyl-1-oxopropyl)amino-3-methyl-1-oxobutyl]aminobenzo[d]isoxazole-6-yl-oxy}butoxy}-3-methoxybenzamide (1w);

24) N,N-diisopropyl-4-{4-{3-[2-(2-amino-3-methyl-1-oxobutyl)amino-3-methyl-1-oxobutyl]aminobenzo[d]isoxazole-6-yl-oxy}butoxy}-3-methoxybenzamide (1x);

25) N,N-diisopropyl-4-{4-{3-[2-(2-amino-4-thiomethyl-1-oxobutyl)amino-3-methyl-1-oxobutyl]aminobenzo[d]isoxazole-6-yl-oxy}butoxy}-3-methoxybenzamide (1y);

More preferable are the compounds represented by the following 1a and 1b.

1) N,N-diisopropyl-4-{4-[3-(2-amino-1-oxoethyl)aminobenzo[d]isoxazole-6-yl-oxy]butoxy}-3-methoxybenzamide (1a);

2) N,N-diisopropyl-4-{4-[3-(2-amino-1-oxopropyl)aminobenzo[d]isoxazole-6-yl-oxy]butoxy}-3-methoxybenzamide (1b).

3-amido-1,2-benzoisoxazole derivatives of the present invention, represented by the formula 1 can be used as optical isomers or pharmaceutically acceptable salts, wherein salts are acidic additive salts prepared by pharmaceutically acceptable free acids. Inorganic acids and organic acids can be used as free acids. Inorganic acids useful in the present invention include, but are not limited to, hydrochloric acid, bromic acid, sulfuric acid, phosphoric acid. Organic acid useful in the present invention include, but are not limited to, citric acid, acetic acid, lactic acid, tartaric acid, maleic acid, umaric acid, gluconic acid, succinic acid, 4-toluenesulfonic acid, galacturonic acid, embonic acid, glutamic acid, methanesulfonic acid or aspartic acid.

The present invention also provides a method for preparing 3-amido-1,2-benzoisoxazole derivatives or their pharmaceutically acceptable acidic additive salts of formula 1, represented by the below Scheme 1, 2.

In particular, the present invention includes methods for preparing 3-amido-1,2-benzoisoxazole derivatives or their pharmaceutically acceptable acidic additive salts represented by formula 1a, in which $R_2$ is hydrogen in accordance with the above formula 1, according to the below Scheme 1.

1) The compound of formula 4 is prepared by condensing the compound of formula 2 with the compound of formula 3a, 2) The protecting group (Boc) of the compound of formula 4 is deprotected by HX.

[Scheme 1]

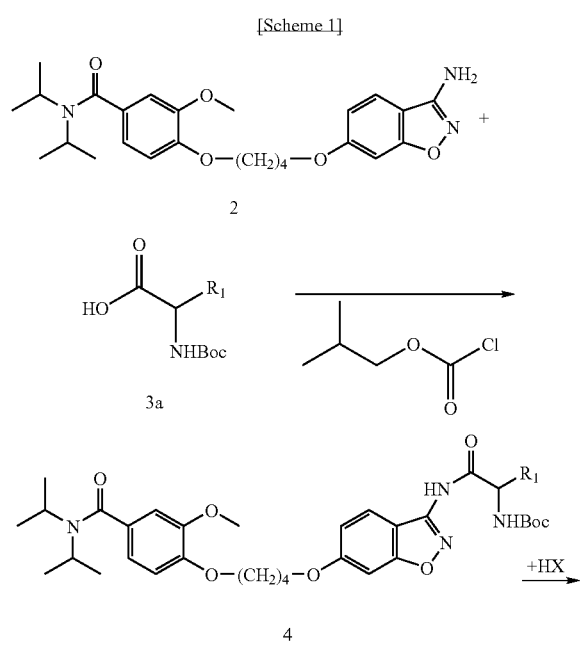

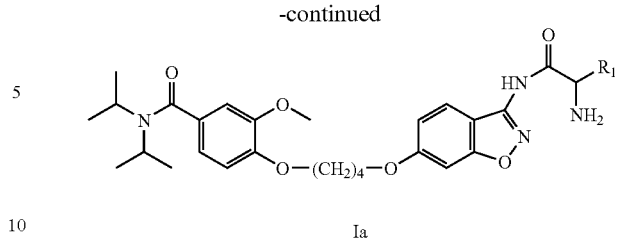

(wherein,
R$_1$ is hydrogen, hydroxymethyl group, straight or branched alkyl group of C$_1$~C$_6$, benzyl group or 2-methylthioethyl group; HX is hydrochloric acid, sulfuric acid, methanesulfonic acid or maleic acid.)

Also, the present invention includes a method for preparing 3-amido-1,2-benzoisoxazole derivatives or their pharmaceutically acceptable acidic additive salts represented by formula 1b, in which R$_2$ is —COCH(NH$_2$)R$_3$ in accordance with the above formula 1, according to the below Scheme 2.

1) A starting material is the compound of formula 1a prepared by the above Scheme 1. The compound of formula 5 is prepared by condensing the above starting material with the compound of formula 3b, 2) The protecting group (Boc) of the compound of formula 5 is deprotected by HX.

[Scheme 2]

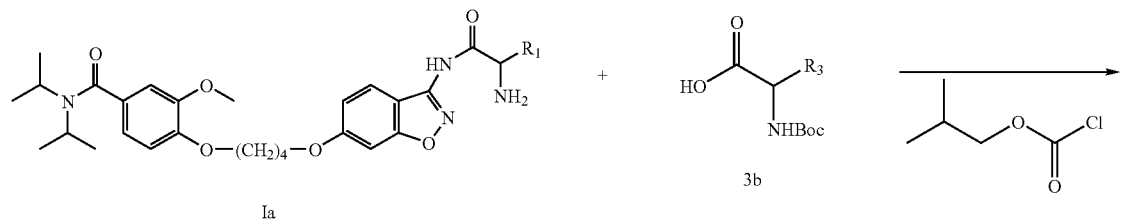

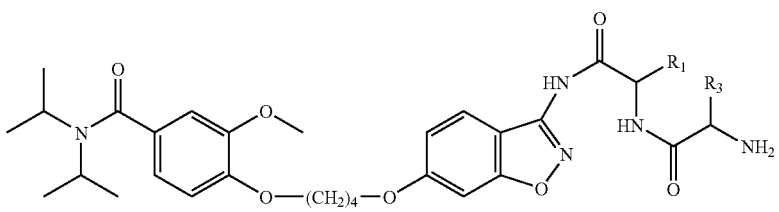

(wherein, $R_1$ is hydrogen, hydroxymethyl group, straight or branched alkyl group of $C_1$~$C_6$, benzyl group or 2-methylthioethyl group; $R_3$ is hydrogen, hydroxymethyl group, straight or branched alkyl group of $C_1$~$C_6$, benzyl group or 2-methylthioethyl group; and HX is hydrochloric acid, sulfuric acid, methanesulfonic acid or maleic acid.)

The preparation method for each step of the present invention will be explained in more detail in the following.

The compound of formula 2 can be prepared by applying the known method by the inventors of the present invention (Korea Patent Application No. 1998-3138).

The compound of the above formula 3a or 3b is selected from the group consisting of N-(t-butoxycarbonyl) glycine, N-(t-butoxycarbonyl)-L-alanine, N-(t-butoxycarbonyl)-L-phenylalanine, N-(t-butoxycarbonyl)-L-valine and N-(t-butoxycarbonyl)-L-methionine.

3-amido-1,2-isoxazole derivatives in accordance with the present invention, including the amino acid residue can increase the oral absorptivity, finally improve their bioavailabilities. Also, compounds including the amino acid residue of the long chain can be subsequently prepared by the same method that starting materials are 3-amido-1,2-benzoisoxazole derivatives, the compound of formula 1a prepared by Scheme 1.

The present invention provides the pharmaceutical composition as an antagonist against LTB-4 receptor, including compounds of the above formula 1 as a effective ingredient.

The present invention also provides the pharmaceutical compositions as inhibitors or therapeutics of osteoporosis, including compounds of the above formula 1 as an effective ingredient.

Pharmaceutical compositions as antagonists of LTB-4 receptor, inhibitors or therapeutics of osteoporosis can be administered through various administration routes in the minimum quantity. Preferably, pharmaceutical compositions as antagonists of LTB-4 receptor, inhibitors or therapeutics of osteoporosis comprise one of 3-amido-1,2-benzoisoxazole derivatives of the formula 1, together with the pharmaceutically acceptable carrier. More particularly, the pharmaceutically acceptable carrier is any of the standard pharmaceutical carriers used in the known formulations, such as sterile solution, tablet, coating tablet and capsule. Conservatively, the carrier is selected from the group of excipient such as starch, milk, glucose, specific clay, gelatin, stearic acid, talc, vegetable oil or fat, gum, glycol, the other known excipients, flavoring agents, pigment additives and other components.

Pharmaceutical compositions as antagonists of LTB-4 receptor, inhibitors or therapeutics of osteoporosis, containing 3-amido-1,2-benzoisoxazole derivatives of the formula 1 according to the present invention is administered, but not is limited, through conservative routes such as oral, intravenous injection, intramuscular injection, transdermal administration. For example, 3-amido-1,2-benzoisoxazole derivatives according to the present invention can be administered to a human body through various oral or parenteral formulations in practically clinical testing. Formulations are prepared by using available additives such as packing agents, bulking agents, binding agents, disintegrants and surfactants, or excipients. Solid formulations for oral administration are provided into various forms including tablets, pills, powders, granules and capsules. Solid formulations are prepared by mixing one or more compounds selected from the group consisting of 3-amido-1,2-benzoisoxazole derivatives of the formula 1, and at least one excipient which is selected from the group consisting of starch, calcium carbonate, sucrose or lactose, gelatin. Also, lubricants such as magnesium stereate talc can be used together with simple diluting agent. Liquid formulations for oral administration are provided into suspension, solution, emulsion and syrup. Various excipients, for example, moistening agent, sweeting agent, aromatic agent and preservative can be included in liquid formulations, together with simple diluting agent, commercially available, such as water, liquid paraffin.

Also, the pharmaceutical composition of the present invention can be administered to a human body parenterally. Perenteral administration is carried out by hypodermic injection, intravenous injection or intramuscular injection. The formulation for parenteral administration is prepared by mixing 3-amido-1,2-benzoxazole derivatives with stabilizing agents or buffering agents in water, formulating solution or suspension and preparing an unit dosage form, such as ample or vial.

In accordance with the present invention, 3-amido-1,2-benzoxazole derivatives of formula 1 are contained in the pharmaceutical compositions in broad ranges. The dose of the medically effective component in accordance with the present invention is selected according to absorptivity of the active component in vivo, activity, excretion rate, age, sex and state of the patients, seriousness of disease under treatment. Generally, the effective component can be administered to a body one time or many times a day, preferably, 10~1000 mg. Accurate dose, administration route and frequency Of the above preparation are dependant on property of the preparation, weight or state of the administrative human and property of specific derivatives.

In accordance with experimental examples of the present invention, pharmacokinetics, the number of the osteoclast cell and area ratio of trabecular bone were examined as for the pharmaceutical composition as an antagonist against LBT-4 receptor, an inhibitor or therapeutics of osteoporosis, which has excellent antagonistic effect of LTB-4 receptor, reduces the number of the osteoclast cell generating osteolysis and stimulates osteogenesis.

The present invention will be explained in more detail with reference to the following examples. However, the following examples are provided only to illustrate the present invention, and the present invention is not limited to them. Purity and structures of those materials according to the present invention are decided by nuclear magnetic resonance spectrum and chromatography.

EXAMPLE 1

Preparation of {5-[4-(4-diisopropylcarbamoyl-2-methoxy-phenoxy)-butoxy]-benzo[d]isoxazole-3-ylcarbamoyl}-methyl-ammonium methane sulfonic acid salt (Step 1): Preparation of t-butoxycarbonyl({6-(4-(4-diisopropylcarbamoyl-2-methoxy-phenoxy)-butoxy]-benzo[d]isoxazole-3-ylcarbamoyl}-methyl)-carbamate 13.5 ml of N-methyl morpholine (122.9 mmol) and 15.9 ml of isobutylchloroformate (122.9 mmol) were added to 21.5 g of N-(t-butoxycarbonyl)glycine (122.9 mmol) dissolved in 200 ml of methylene chloride at 0° C., stirred for 5 min. Thereafter, according to Scheme 1, 14.0 g of the compound of formula 2 (30.7 mmol) (prepared by the known method, Korea Patent Application No. 1998-3138) was added to the above mixture, stirred at the room temperature for 15 hours. The stirred mixture was washed with sodium bicarbonate solution, the resultant organic layer was dried with anhydrous magnesium sulfate, the solvent of the organic layer was removed to obtain 13.5 g of t-butoxycarbonyl({6-[4-(4-diisopropylcarbamoyl-2-methoxy-phenoxy)-butoxy]-benzo[d]isoxazole-3-ylcarbamoyl}-methyl)-carbamate. (yield 72%).

R$_f$: 0.33 (Ethyl acetate:hexane=2:1)

(Step 2): Preparation of (5-[4-(4-diisopropylcarbamoyl-2-methoxy-phenoxy)-butoxy]-benzo[d]isoxazole-3-ylcarbamoyl)-methyl-ammonium methane sulfonic acid salt.

13.3 g of the compound (21.7 mmol) prepared in the above step was dissolved in 100 ml of methylene chloride, 7.0 ml of methanesulfonic acid (108 mmol) was added slowly thereto and stirred for 15 min. Thereafter diethyl ether was added slowly thereto to give a precipitation, filtered under reduced pressure to obtain the solid residue. After the above residue was purified by column chromatography (methylene chloride:methanol=8:1), 9.5 g of the above title compound was obtained (yield: 71%).

R$_f$: 0.03 (ethyl acetate:hexane=2:1)

$^1$H-NMR (CDCl$_3$): δ 1.20~1.40(m, 12H), 1.90(m, 4H), 3.63(br, 2H), 3.74(s, 3H), 3.93(S, 2H), 4.10(m, 4H), 6.77~7.27(m, 5H), 7.89(d, 1H)

EXAMPLE 2

Preparation of (1S)-1-{5-[4-(4-diisopropylcarbamoyl-2-methoxy-phenoxy)-butoxy]-benzo[d]isoxazole-3-ylcarbamoyl)-ethyl-ammonium methane sulfonic acid salt According to the same method as in EXAMPLE 1, N-(t-butoxycarbonyl)-L-alanine was used in place of N-(t-butoxycarbonyl)glycine, the above title compound was obtained (yield: 71%).

R$_f$: 0.45 (methylene chloride:methanol=5:1)

$^1$H-NMR (CDCl$_3$): δ 1.00~1.50 (m, 15H), 1.89(m, 4H), 3.58~3.75(m, 6H), 4.02~4.24(m, 4H), 6.76~7.20(m, 5H), 7.92(d, 1H)

EXAMPLE 3

Preparation of (1S)-1-(5-[4-(4-diisopropylcarbamoyl-2-methoxy-phenoxy)-butoxy]-benzo[d]isoxazole-3-ylcarbamoyl}-2-phenyl-ethyl-ammonium methane sulfonic acid salt According to the same method as in EXAMPLE 1, N-(t-butoxycarbonyl)-L-phenylalanine was used in place of N-(t-butoxycarbonyl)glycine, the above title compound was obtained (yield: 65%).

R$_f$: 0.57 (methylene chloride:methanol=8:1)

$^1$H-NMR (CDCl$_3$): δ 1.23 (m, 12H), 1.90(m, 4H), 2.77~3.05(m, 2H), 3.30~3.78(m, 6H), 4.02~4.14(m, 4H), 6.77~6.96(m, 4H), 7.19~7.26(m, 6H), 7.84(d, 1H)

EXAMPLE 4

Preparation of (1S)-1-{5-[4-(4-diisopropylcarbamoyl-2-methoxy-phenoxy)-butoxy]-benzo[d-]isoxazole-3-ylcarbamoyl)-2-methyl-propyl-ammonium methane sulfonic acid salt According to the same method as in Example 1, N-(t-butoxycarbonyl)-L-valine was used in place of N-(t-butoxycarbonyl)glycine, the above title compound was obtained (yield: 73%).

R$_f$: 0.02 (ethyl acetate:hexane=2:1)

$^1$H-NMR (CDCl$_3$): δ 0.76~0.95(m, 6H), 1.24(m, 12H), 1.89(m, 5H), 3.06(m, 1H), 3.56~3.83(m, 5H), 4.03~4.14(m, 4H), 6.76~6.96(m, 4H), 7.20(s, 1H), 7.89(d, 1H)

EXAMPLE 5

Preparation of (1S)-1-(5-[4-(4-diisopropylcarbamoyl-2-methoxy-phenoxy)-butoxy]-benzo[d]isoxazole-3-ylcarbamoyl}-3-methylsulfanyl-propyl-ammonium methane sulfonic acid salt According to the same method as in EXAMPLE 1, N-(t-butoxycarbonyl)-L-methionine was used in place of N-(t-butoxycarbonyl)glycine, the above title compound was obtained (yield: 75%).

R$_f$: 0.68 (methylene chloride:methanol=8:1)

$^1$H-NMR (CDCl$_3$): δ 0.78~1.11(m, 12H), 1.77~2.49(m, 11H), 2.80~3.63(m, 5H), 3.7~4.04(m, 5H), 6.67~6.86 (m, 4H), 7.12(s, 1H), 7.77(d, 1H)

EXAMPLE 6

Preparation of [({6-[4-(4-diisopropylcarbamoyl-2-methoxy-phenoxy)-butoxy]-benzo[d]isoxazole-3-ylcarbamoyl)-methyl)-carbamoyl]-methyl-ammonium methane sulfonic acid salt (Step 1): Preparation of t-butoxycarbonyl([({6-[4-(4-diisopropylcarbamoyl-2-methoxy-phenoxy)-butoxy]-benzo[d]isoxazole-3-ylcarbamoyl}-methyl)-carbamoyl]-methyl}-carbamate 288 ml of N-methyl morpholine (2.624 mmol) and 127 ml of isobutylchloroformate (0.984 mmol) were added to 172 mg of N-(t-butoxycarbonyl)glycine (0.984 mmol) dissolved in 20 ml of methylene chloride at 0° C., stirred for 15 min. Thereafter, 500 mg of the compound of EXAMPLE 1 (0.82 mmol) was added to the above mixture, stirred at the room temperature for 1 hour. After stirred, the resulting mixture was diluted with methylene chloride, washed with distilled water. The resultant organic layer was dried with anhydrous magnesium sulfate, the solvent of the organic layer was removed to obtain 13.5 g of t-butoxycarbonyl{[({6-[4-(4-diisopropylcarbamoyl-2-methoxy-phenoxy)-butoxy]-benzo[d]isoxazole-3-ylcarbamoyl}-methyl)-carbamoyl]-methyl}-carbamate. (yield: 72%).

R$_f$: 0.40 (ethyl acetate:hexane=2:1)

(Step 2): Preparation of [(16-[4-(4-diisopropylcarbamoyl-2-methoxy-phenoxy)-butoxy]-benzo[d]isoxazole-3-ylcarbamoyl]-methyl)-carbamoyl]-methyl-ammonium methane sulfonic acid salt The compound prepared in the above step 1 was dissolved in 12 ml of methylene chloride, 0.16 ml of methane sulfonic acid (2.42 mmol) was added slowly thereto and stirred for 15 min. Thereafter, diethyl ether was added slowly thereto to give a precipitation, filtered under reduced pressure to obtain the solid residue. After the above residue was purified by column chromatography (methylene chloride:methanol=8:1), 400 mg of the above title compound was obtained (yield: 50%).

R$_f$: 0.04 (ethyl acetate:hexane=2:1)

$^1$H-NMR (CDCl$_3$): δ 1.10~1.40(m, 12H), 1.89(m, 4H), 3.66~3.74(m, 5H), 3.90~4.15(m, 8H), 6.77~7.22(m, 5H), 7.87(d, 1H)

EXAMPLE 7

Preparation of (1S)-1-[({6-[4-(4-diisopropylcarbamoyl-2-methoxy-phenoxy)-butoxy]-benzo[d]isoxazole-3-ylcarbamoyl}-methyl)-carbamoyl]-ethyl-ammonium methane sulfonic acid salt According to the same method as in EXAMPLE 6, N-(t-butoxycarbonyl)-L-alanine was used in place of N-(t-butoxycarbonyl)glycine, the above title compound was obtained (yield: 71%).

$R_f$: 0.02 (ethyl acetate:hexane=2:1)
$^1$H-NMR (CDCl$_3$): δ 0.84(d, 3H), 1.10~1.40(m, 12H), 1.88(m, 4H) 3.61~3.73(m, 5H), 3.82 (m, 1H), 4.02~4.13(m, 6H), 6.77~7.19(m, 5H), 7.88(d, 1H)

EXAMPLE 8

Preparation of (1S)-1-[({6-[4-(4-diisopropylcarbamoyl-2-methoxy-phenoxy)-butoxy]-benzo[d]isoxazole-3-ylcarbamoyl}-methyl)-carbamoyl]-2-phenyl-ethyl-ammonium methane sulfonic acid salt According to the same method as in EXAMPLE 6, N-(t-butoxycarbonyl)-L-phenylalanine was used in place of N-(t-butoxycarbonyl)glycine, the above title compound was obtained (yield: 78%).

$R_f$: 0.01 (ethyl acetate:hexane=2:1)
$^1$H-NMR (CDCl$_3$): δ 1.10~1.40(m, 12H), 1.89(m, 4H), 2.96~3.13(m, 2H), 3.74~3.92(m, 6H), 4.06~4.13(m, 6H), 6.77~7.30(m, 10H), 7.87(d, 1H)

EXAMPLE 9

Preparation of (1S)-1-[({6-[4-(4-diisopropylcarbamoyl-2-methoxy-phenoxy)-butoxy]-benzo[d]isoxazole-3-ylcarbamoyl}-methyl)-carbamoyl]-2-methyl-propyl-ammonium methane sulfonic acid salt According to the same method as in EXAMPLE 6, N-(t-butoxycarbonyl)-L-valine was used in place of N-(t-butoxycarbonyl)glycine, the above title compound was obtained (yield: 25%).

$R_f$: 0.13 (methylene chloride:methanol=8:1)
$^1$H-NMR (CDCl$_3$): δ 0.80(d, 3H), 0.89(d, 3H), 1.10~1.40 (m, 12H), 1.90(m, 5H), 3.03(d, 1H), 3.72(br, 2H), 3.75(s, 3H), 4.03~4.15(m, 6H), 6.77~6.97(m, 4H), 7.21(S, 1H), 7.86(s, 1H)

EXAMPLE 10

Preparation of (1S)-1-[({6-[4-(4-diisopropylcarbamoyl-2-methoxy-phenoxy)-butoxy]-benzo[d]isoxazole-3-ylcarbamoyl}-methyl)-carbamoyl]-3-methyl sulfanyl-propyl-ammonium methane sulfonic acid salt According to the same method as in EXAMPLE 6, N-(t-butoxycarbonyl)-L-methionine was used in place of N-(t-butoxycarbonyl)glycine, (1S)-1-[({6-[4-(4-diisopropylcarbamoyl-2-methoxy-phenoxy)-butoxy]-benzo[d]isoxazole-3-ylcarbamoyl}-methyl)-carbamoyl]-3-methyl sulfanyl-propyl-ammonium methane sulfonic acid salt was obtained.

$R_f$: 0.20 (methylene chloride:methanol=8:1)
$^1$H-NMR (CDCl$_3$): δ 1.10~1.40(m, 12H), 1.91~2.07(m, 6H), 2.30~2.70(m, 5H), 3.40~3.78(m, 6H), 4.00~4.26(m, 6H), 6.83~7.23(m, 5H), 7.87(d, 1H)

EXAMPLE 11

Preparation of ((1S)-1-{6-[4-(4-diisopropylcarbamoyl-2-methoxy-phenoxy)-butoxy]-benzo[d]isoxazole-3-ylcarbamoyl}-ethyl-carbamoyl)-methyl-ammonium methane sulfonic acid salt (1S)-1-{5-[4-(4-diisopropylcarbamoyl-2-methoxy-phenoxy)-butoxy]-benzo[d]isoxazole-3-ylcarbamoyl}-ethyl-ammonium methane sulfonic acid salt, the compound of EXAMPLE 2, was used as a starting material in place of {5-[4-(4-diisopropylcarbamoyl-2-methoxy-phenoxy)-butoxy]-benzo[d]isoxazole-3-ylcarbamoyl}-methyl-ammonium methane sulfonic acid used in the above EXAMPLE 6. According to the same method as in EXAMPLE 6, N-(t-butoxycarbonyl)glycine was used, the above title compound was obtained. (yield: 72%)

$R_f$: 0.02 (ethyl acetate:hexane=2:1)
$^1$H-NMR (CDCl$_3$): δ 1.10~1.38(m, 12H), 1.39(d, 3H), 1.89(m, 4H), 3.63~3.74(m, 7H), 4.03~4.15(m, 4H), 4.60(m, 1H), 6.77~7.22(m, 5H), 7.84(d, 1H)

EXAMPLE 12

Preparation of (1S)-1-((1S)-1-{6-[4-(4-diisopropylcarbamoyl-2-methoxy-phenoxy)-butoxy]-benzo[d]isoxazole-3-ylcarbamoyl}-ethyl-carbamoyl)-ethyl-ammonium methane sulfonic acid salt According to the same method as in EXAMPLE 11, N-(t-butoxycarbonyl)-L-alanine was used in place of N-(t-butoxycarbonyl)glycine, the above title compound was obtained (yield: 69%)

$R_f$: 0.02 (ethyl acetate:hexane=2:1)
$^1$H-NMR (CDCl$_3$): δ 1.05~1.40(m, 18H), 1.89(m, 4H), 3.70(m, 2H), 3.74(s, 3H), 3.87(q, 1H), 4.03~4.15(m, 4H), 4.56(m, 1H), 6.76~6.97(m, 4H), 7.21(S, 1H), 7.84(d, 1H)

EXAMPLE 13

Preparation of (1S)-1-((1S)-1-{6-[4-(4-diisopropylcarbamoyl-2-methoxy-phenoxy)-butoxy]-benzo[d]isoxazole-3-ylcarbamoyl}-ethyl-carbamoyl)-2-phenyl-ethyl-ammonium methane sulfonic acid salt According to the same method as in EXAMPLE 11, N-(t-butoxycarbonyl)-L-phenylalanine was used in place of N-(t-butoxycarbonyl)glycine, the above title compound was obtained (yield: 76%).

$R_f$: 0.05 (ethyl acetate:hexane=2:1)
$^1$H-NMR (CDCl$_3$): δ 1.00~1.40(m, 15H), 1.84(m, 4H), 2.95~3.10(m, 2H), 3.56(m, 2H), 3.69(s, 3H), 3.97~4.09(m, 5H), 4.57(m, 1H), 6.76~7.50(m, 10H), 7.81(d, 1H)

EXAMPLE 14

Preparation of (1S)-1-((1S)-1-{6-[4-(4-diisopropyl-carbamoyl-2-methoxy-phenoxy)-butoxy]-benzo[d]isoxazole-3-ylcarbamoyl}-ethyl-carbamoyl)-2-methyl-propyl-ammonium methane sulfonic acid salt According to the same method as in EXAMPLE 11, N-(t-butoxycarbonyl)-L-valine was used in place of N-(t-butoxycarbonyl)glycine, the above title compound was obtained (yield: 87%).

$R_f$: 0.02 (ethyl acetate:hexane=2:1)
$^1$H-NMR (CDCl$_3$): δ 1.31~1.79(m, 21H), 2.27(m, 4H), 2.49(m, 1H), 3.56(m, 1H), 3.96~4.09(m, 5H), 4.42(m, 4H), 4.70~4.95(m, 1H), 7.15~7.32(m, 5H), 8.10(d, 1H)

EXAMPLE 15

Preparation of (1S)-1-((1S)-1-{6-[4-(4-diisopropyl-carbamoyl-2-methoxy-phenoxy)-butoxy]-benzo[d]isoxazole-3-ylcarbamoyl}-ethyl-carbamoyl)-3-methyl sulfanyl-propyl-ammonium methane sulfonic acid salt According to the same method as in EXAMPLE 11, N-(t-butoxycarbonyl)-L-methionine was used in place of N-(t-butoxycarbonyl)glycine, the above title compound was obtained (yield: 48%).

$R_f$: 0.03 (ethyl acetate:hexane=2:1)
$^1$H-NMR (CDCl$_3$): δ 1.00~1.40(m, 15H), 1.80~2.00(m, 6H), 2.33~2.53(m, 5H), 3.56(m, 2H), 3.69(s, 3H), 3.87~4.09 (m, 5H), 4.51(m, 1H), 6.70~7.15(m, 5H), 7.77(d, 1H)

EXAMPLE 16

Preparation of (1S)-1-[({6-[4-(4-diisopropylcarbamoyl-2-methoxy-phenoxy)-butoxy]-benzo[d]isoxazole-3-ylcarbamoyl}-2-phenyl-ethyl-carbamoyl)-methyl-ammonium methane sulfonic acid salt (1S)-1-{5-[4-(4-diisopropylcarbamoyl-2-methoxy-phenoxy)-butoxy]-benzo[d]isoxazole-3-ylcarbamoyl}-2-phenyl-ethyl-ammonium methane sulfonic acid salt, the compound of EXAMPLE 3, was used as a starting material in place of {5-[4-(4-diisopropylcarbamoyl-2-methoxy-phenoxy)-butoxy]-benzo[d]isoxazole-3-ylcarbamoyl}-methyl-ammonium methane sulfonic acid used in the above EXAMPLE 6. According to the same method as in EXAMPLE 6, N-(t-butoxycarbonyl)glycine was used, the above title compound was obtained (yield: 80%).

$R_f$: 0.18 (methylene chloride:methanol=8:1)
$^1$H-NMR (CDCl$_3$): δ 1.09~1.39(m, 12H), 1.92(m, 4H), 3.03(m, 2H), 3.65~3.89(m, 5H), 4.04~4.15(m, 6H), 4.91(m, 1H), 6.79~7.34(m, 10H), 7.82(d, 1H)

EXAMPLE 17

Preparation of (1S)-1-((1S)-1-{6-[4-(4-diisopropyl-carbamoyl-2-methoxy-phenoxy)-butoxy]-benzo[d]isoxazole-3-ylcarbamoyl}-2-phenyl-ethyl-carbamoyl)-ethyl-ammonium methane sulfonic acid salt According to the same method as in EXAMPLE 16, N-(t-butoxycarbonyl)-L-alanine was used in place of N-(t-butoxycarbonyl)glycine, the above title compound was obtained (yield: 47%).

$R_f$: 0.09 (methylene chloride:methanol=8:1)
$^1$H-NMR (CDCl$_3$): δ 1.24~1.37(m, 15H), 1.89(m, 4H), 2.98~3.15(m, 2H), 3.15~3.84(m, 6H), 4.03~4.15(m, 4H), 4.68(m, 1H), 6.77~7.37(m, 10H), 7.77(d, 1H)

EXAMPLE 18

Preparation of (1S)-1-((1S)-1-{6-[4-(4-diisopropyl-carbamoyl-2-methoxy-phenoxy)-butoxy]-benzo[d]isoxazole-3-ylcarbamoyl}-2-phenyl-ethyl-carbamoyl)-2-methyl-propyl-ammonium methane sulfonic acid salt According to the same method as in EXAMPLE 16, N-(t-butoxycarbonyl)-L-valine was used in place of N-(t-butoxycarbonyl)glycine, the above title compound was obtained (yield: 68%).

$R_f$: 0.54 (methylene chloride:methanol=8:1)
$^1$H-NMR (CDCl$_3$): δ 0.78~0.89(m, 6H), 1.09~1.39(m, 12H), 1.83~1.90(m, 5H), 3.00~3.17(m, 2H), 3.59-3.74(m, 2H), 3.76~3.84(m, 4H), 4.03~4.15(m, 4H), 4.91(m, 1H), 6.78~7.33(m, 10H), 7.79(d, 1H)

EXAMPLE 19

Preparation of (1S)-1-((1S)-1-{6-[4-(4-diisopropyl-carbamoyl-2-methoxy-phenoxy)-butoxy]-benzo[d]isoxazole-3-ylcarbamoyl}-2-phenyl-ethyl-carbamoyl)-3-methyl sulfanyl-propyl-ammonium methane sulfonic acid salt According to the same method as in EXAMPLE 16, N-(t-butoxycarbonyl)-L-methionine was used in place of N-(t-butoxycarbonyl)glycine, the above title compound was obtained (yield: 73%).

$R_f$: 0.60 (methylene chloride:methanol=8:1)
$^1$H-NMR (CDCl$_3$): δ 1.10~1.40(m, 12H), 1.80~2.02(m, 6H), 2.50~2.80(m, 7H), 3.60~4.12(m, 10H), 6.76~7.39(m, 10H), 7.76(d, 1H)

PREPARATION EXAMPLE 1

Preparation of the Liquid Formulation for Injection

The liquid formulation for injection, containing 10 mg of active component was prepared by the following process.

1 g of the compound of EAMPLE 1, 0.6 g of sodium chloride and 0.1 g of ascorbic acid were dissolved in distilled water, giving 100 ml of solution. The solution was placed in bottle, sterilized by heating at 20° C. for 30 min.

The above liquid formulation for injection was comprising;

| | |
|---|---|
| the compound of EXAMPLE 1 | 1.0 g |
| sodium chloride | 0.6 g |
| ascorbic acid | 0.1 g |
| distilled water | conditioned-weight |

PREPARATION EXAMPLE 2

Method for Preparation of Tablets

The tablet containing 15 mg of active component was prepared by the following process.

250 g of hydrochloride salt of the compound of EXAMPLE 1 was mixed with 175.9 g of lactose, 180 g of potato starch and 32 g of colloidal silicic acid. 10% gelatin solution was added to the above mixture. The resultant mixture was grinded, passed through sieve of 14 mesh and dried. 160 g of potato starch, 50 g of talc and 5 g of magnesium stereate were added thereto, giving the tablet.

The above tablet was comprising;

| | |
|---|---|
| hydrochloride salt of the compound of EXAMPLE 1 | 250 g |
| lactose | 175.9 g |
| potato starch | 180 g |
| colloidal silicic acid | 32 g |
| 10% gelatin solution | |
| potato starch | 160 g |
| talc | 50 g |
| magnesium stearate | 5 g |

As for the compound of formula 1 according to the present invention, various pharmacological efficacies were examined through the following tests.

EXPERIMENTAL EXAMPLE 1

Pharmacokinetics Test

Male white rats (Sprague-Dawley) having body weights of 230~260 g were used, 3~4 rats were tested for a drug. Rats were fasted for 18~20 hours before the drug was administered. The weight of rat was measured on the day of the experiment, the drug was administered orally to the rats according to dosage. After administration, rats were lightly anesthetized with diethyl ether. At a, 0.17, 0.5, 1.0, 1.5, 3.0, 5.0, 8.0 hours, the blood was collected from orbit vein of the rats by canulation. The collected blood was centrifuged, and the plasma was isolated. To determine concentration of the drug in plasma, HPLC was carried out as follows. Acetonitrile containing internal standard substance and the isolated plasma was mixed in the same amount, followed by centrifuging at 12,000 rpm. The supernatent was applied to HPLC, bioavailability of the compounds prepared in EXAMPLES was measured by analyzing a plasma concentration of the compound of formula 2.

Pharmacokinetics parameters were measured by noncompartmental analysis, using WinNolin (ver. 1.0 Scientific Consulting Inc., USA). Time and maximum plasma concentration were registered by observed data, half life was calculated by linear regression analysis of terminal elimination phase. The results are given in table 1, below.

TABLE 1

Pharmacokinetics test as therapeutics of osteoporosis in rats

| Compounds | Dosage (mg/kg) | vehicle[a] | $C_{max}$ (μg/ml) | $T_{max}$ (hour) | $T_{1/2}$ (hour) | Total AUC (μg · hr/ml) |
|---|---|---|---|---|---|---|
| EX. 1 | 50 | DW | 1.53 | 0.50 | 2.29 | 5.72 |
| EX. 1 | 100 | DW | 1.51 | 0.50 | 5.58 | 11.08 |
| EX. 2 | 50 | DW | 1.83 | 0.50 | 1.27 | 8.75 |
| EX. 3 | 50 | DW | 1.18 | 0.50 | 1.51 | 3.69 |
| EX. 4 | 50 | DW | 0.98 | 0.50 | 1.11 | 2.45 |
| EX. 5 | 50 | DW | 1.36 | 0.50 | 4.29 | 7.63 |
| EX. 6 | 50 | DW | 0.16 | 0.25 | 1.66 | 0.38 |
| EX. 9 | 50 | DW | 0.50 | 0.25 | 0.54 | 0.51 |
| EX. 10 | 50 | DW | 0.24 | 0.25 | ND | ND |
| EX. 11 | 50 | DW | 0.96 | 0.25 | 1.17 | 1.70 |
| EX. 12 | 50 | DW | 0.23 | 0.25 | 2.57 | 0.59 |
| EX. 13 | 50 | DW | 1.00 | 0.25 | 1.69 | 1.28 |

TABLE 1-continued

Pharmacokinetics test as therapeutics of osteoporosis in rats

| Compounds | Dosage (mg/kg) | vehicle[a] | $C_{max}$ (μg/ml) | $T_{max}$ (hour) | $T_{1/2}$ (hour) | Total AUC (μg · hr/ml) |
|---|---|---|---|---|---|---|
| EX. 14 | 50 | DW | 0.44 | 0.25 | 0.43 | 0.41 |
| EX. 17 | 50 | DW | 0.26 | 0.25 | 2.73 | 1.43 |
| Formula 2 | 50 | DW + T | 0.08 | 1.50 | ND | ND |
| Formula 2 | 50 | DMSO | 0.47 | 0.17 | 0.32 | 0.19 |

[a]DW: distilled water, T: tween 80, DMSO: dimethyl sulfoxide
ND: not determined
AUC: Area Under Curve As shown in Table 1, compared to 3-amino-1,2-benzoisoxazole derivative of formula 2 (KR 1998-71076A), 3-amido-1,2-benzoisoxazole derivatives or pharmaceutically acceptable acidic salts prepared by applying amino acid residue to amine group of 3-amido-1,2-benzoisoxazole according to the present invention had excellent effect in a drug absorption to a body, compared to 3-amino-1,2-benzoisoxazole derivatives of formula 2 (Korea Patent Application No. 1998-3138).

The compound of formula 2 dissolved in Solution of distilled water and tween 80, when an amount of 50 mg per kg was administered to a rat, no drug was absorbed to a rat. When administered the same amount dissolved in dimethylsulfoxide to a rat, maximum plasma concentration ($C_{max}$) was 0.47 μg/ml at 0.17 hour after administration, plasma concentration was observed to be very low. When the same amount of the compound of example 1 was administered to a rat, maximum plasma concentration ($C_{max}$) was 1.53 μg/ml at 0.5 hour after administration, plasma concentration was very increased relative to the compound of formula 2. Also, it can be easily used in vivo since it can be administered by being dissolved in distilled water not organic solvents such as dimethyl sulfoxide. Also, in case of the compound of formula 2, half life ($T_{1/2}$) and total area-under-curve (AUC) as index of the bioavailbility were 0.32 hour and 0.19 μg hr/ml, respectively. However, as for the compound of example 1, half life ($T_{1/2}$) and total area-under-curve (AUC) were 2.29 hour and 5.72 μg·hr/ml, respectively. Consequently, the compound of the present invention improved the bioavailbility of the drug. When doubled the dosage of the compound of formula 1, in an amount of 100 mg per kg, half life ($T_{1/2}$) and total area-under-curve (AUC) were 5.58 hour and 11.08 μg·hr/ml, respectively. All the parameters of the compound of formula 1 were increased two times, consequently internal distribution of the drug was increased in proportion to the increase of dosage.

The compound of EXAMPLE 2 showed similar pharmacokinetic result of the compound of EXAMPLE 1. As shown in Table 1, maximum plasma concentration ($C_{max}$) was 1.83 μg/ml at 0.5 hour after administration, half life ($T_{1/2}$) and total area-under-curve (AUC) were 1.27 hour and 8.75 μg hr/ml, respectively. The compound of EXAMPLE 2 had excellent effect in a drug absorptivity to a body, relative to the compound of EXAMPLE 1.

On the other hand, when the compound of EXAMPLE 6 and 11 were administered to a rat in an amount of 50 mg per kg, maximum plasma concentration was 0.16 and 0.96 respectively, which showed a significant difference from formula 2. However, total area-under-curve (AUC) was 0.38 μg·hr/ml and 1.70 μg hr/ml respectively, higher than that of the compound of formula 2. Total are-under-curve (AUC) of all the examples of the present invention were higher than that of the compound of formula 2.

All the examples of the present invention increased maximum plasma concentration ($C_{max}$), half life ($T_{1/2}$) and total area-under-curve (AUC) as well as oral absorption, relative to the compound of formula 2 and improved absorption of the body system. The compounds of the present invention improved bioavailablity than the compound of formula 2 by applying amino acid residue to the amine group.

PREPARATION EXAMPLE 2

Therapeutic Value of the Effect to Osteoporotic Rat Induced by Ovariectomy

To investigate therapeutic value of the osteoporosis to ovariectomized rats, change in the number of osteoclast cell and area ratio of trabecular bone (volume %) were measured.

After 25 female white rats purchased from Chales River (Japan) were adjusted to a new environment, temperature of 20~25° C. and relative humidity of 30~35%. The 5 rats were positioned in a hutch, feed (Sam Yang corporation) and water were supplied to the rats. 20 rats had the operation for the removal of an ovary, 5 rats had the Sham operation for opening and suturing the abdominal cavity, used as Sham control group.

Also, to compare drug efficacies of EXAMPLE and the compound of formula 2, 5 rats removed of the ovary were used as experimental group. The compound of formula 2 was dissolved in injectable distilled water and administered to the rats orally in an amount of 100 mg per kg for 40 days from 10 weeks after ovariectomy or Sham-operation, using oral sonde. 5 ml/kg was administered to the rats. To compare with the compound of formula 2, the compounds of EXAMPLE 1 or 2 were prepared in the same concentration as the compound of formula 2, dissolved in PEG 100 solution (PEG 100:tween 80:water=2:3:15) and administered through intramuscular injection. 5 ml/kg was administered to the rats.

After administration terminated, the femur and tibia were removed from the animals, and fixed in 10% neutral formalin. The fixed tissue was decalcified in a solution (solution mixed 24.4% formic acid and 0.5 N sodium hydroxide) for 5 days, embedded in paraffin and 3~4 μm sections were prepared. After that prepared section were dyed by hematoxylin-eosin.

To investigate the effect of the compound of EXAMPLE 1 and 2 in the osteoporosis, change in the number of osteoclast cell and area ratio of trabecular bone existed in the tissue section was observed. Change in the number of osteoclast cell was calculated by mean±standard deviation through the number of the osteoclast cell existed within 1 mm$^2$ area at the 10 sections. The experiment group administered was compared with the control group not and Sham group. The results were shown in Table 2.

Also, the area ratio of trabecular bone was calculated at the section of the femur and tibia respectively, through the equation. The results were shown in Table 3.

$$\text{area ratio of trabecular bone} = \frac{\text{area of trabecular bone}}{\text{area of all the bone}} \times 100 \quad \text{[Equation]}$$

TABLE 2

| Administration | Change in the number of osteoclast cell | | | |
|---|---|---|---|---|
| | femur | | Tibia | |
| Material | Right | Left | Right | Left |
| EX. 1 | 4.90 ± 1.52*,# | 5.10 ± 2.38*,# | 5.30 ± 2.00*,# | 5.40 ± 2.76*,## |
| EX. 2 | 5.00 ± 1.51*,## | 4.50 ± 1.69*,# | 5.63 ± 1.30*,# | 4.50 ± 1.60*,# |
| Sham | 2.50 ± 1.18 | 2.00 ± 1.05 | 2.00 ± 1.05 | 1.70 ± 1.06 |
| Control group | 7.70 ± 2.83* | 8.50 ± 2.80* | 8.80 ± 2.25* | 8.60 ± 2.88* |

*a significant level compared to Sham ($p < 0.01$),
a significant level compared to control group ($p < 0.01$) and
a significant level compared to control group ($p < 0.05$)

TABLE 3

| | Change of the area ratio of trabecular bone | | | |
|---|---|---|---|---|
| | Femur | | Tibia | |
| | Right | Left | Right | Left |
| EX. 1 | 34.59 ± 8.77*,# | 34.87 ± 3.41*,## | 34.58 ± 14.52* | 30.22 ± 6.31* |
| Ex. 2 | 33.93 ± 3.71*,## | 41.95 ± 8.78# | 35.58 ± 9.55*,## | 40.12 ± 7.20**,# |
| Sham | 54.09 ± 8.37 | 50.88 ± 6.38 | 52.44 ± 6.02 | 57.74 ± 9.25 |
| Control group | 23.76 ± 7.07* | 25.09 ± 7.61* | 21.22 ± 6.44* | 23.11 ± 4.57* |
| Formula 2 | 31.69 ± 9.83* | 31.38 ± 7.88*,## | 29.35 ± 11.37* | 28.22 ± 5.54* |

*a significant level compared to Sham ($p < 0.01$),
a significant level compared to control group ($p < 0.01$) and
a significant level compared to control group ($p < 0.05$)

As shown in Table 1 and Table 2, when the compounds of EXAMPLE 1 and 2 were administered to the osteoporotic rats induced by ovariectomy, it was observed that the osteoclast cells inducing the osteolysis were significantly decreased in the group administered the drug and the area ratio of trabecular bone was excellently increased compared to the control group. It was observed that the compounds of EXAMPLE 1 and 2 had considerable therapeutic value to the rats induced the osteoporosis by ovariectomy. Also, as shown in Table 3, the compounds of EXAMPLE 1 and 2 increased the area ratio of the trabecular bone, had more distinguished therapeutic value than the compound of formula 2.

INDUSTRIAL APPLICABILITY

As stated above, in accordance with the present invention, 3-amido-1,2-benzoisoxazole derivatives of formula 1 prepared by introducing amino acid residue to the amine residue of 3-amido-1,2-benzoisoxazole, or their pharmaceutically acceptable acidic additive salts not only show increase in the solubility in water, but also increase the highest value of plasma concentration after administration, and improve the bioavailability by showing an increased result in the half life and total AUC value. In addition, antagonism against LTB-4 receptor is superior, and the number of the osteoclast cell generating osteolysis significantly decreased. Further, they are also very efficient as pharmaceutical compositions used for inhibiting or treating osteoporosis due to the increase of area of bone.

What is claimed is:
1. 3-amido-1,2-benzoisoxazole derivatives or pharmaceutically acceptable acidic additive salts, represented by the following formula 1.

[formula 1]

wherein,
R$_1$ is hydrogen, hydroxymethyl group, straight or branched alkyl group of C$_1$~C$_6$, benzyl group or 2-methylthioethyl group;
R$_2$ is hydrogen or —COCH (NH$_2$) R$_3$; and
R$_3$ is hydrogen, hydroxymethyl group, straight or branched alkyl group of C$_1$~C$_6$, benzyl group or 2-methylthioethyl group.
2. 3-amido-1,2-benzoisoxazole derivatives or pharmaceutically acceptable acidic additive salts according to claim 1, wherein R$_1$ is hydrogen, methyl group, isopropyl group, isobutyl group, benzyl group or 2-methylthioethyl group.

3. The method for preparing 3-amido-1,2-benzoisoxazole derivatives or pharmaceutically acceptable acidic additive salts represented by formula 1a, which comprises the steps according to Scheme 1:
1) preparing a compound of formula 4 by condensing a compound of formula 2 with the compound of formula 3a,
2) preparing a compound of formula 1a by deprotecting a protecting group of the compound of formula 4 by HX.

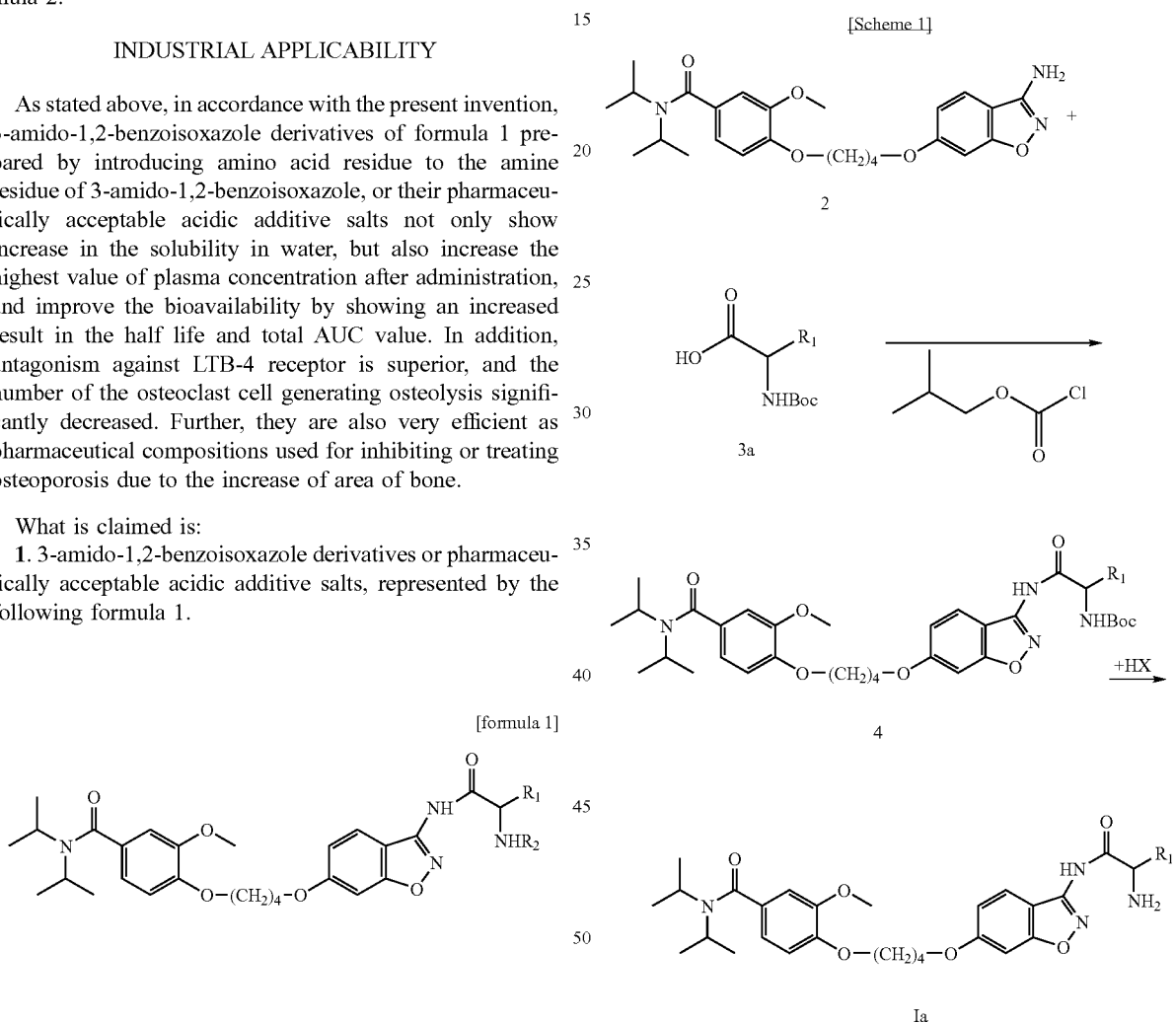

[Scheme 1]

(wherein, R$_1$ is hydrogen, hydroxymethyl group, straight or branched alkyl group of C$_1$ ~C$_6$, benzyl group or 2-methylthioethyl group; HX is hydrochloric acid, sulfuric acid, methane sulfonic acid or maleic acid.)

4. The method for preparing 3-amido-1,2- benzoisoxazole derivatives or pharmaceutically acceptable acidic additive salts represented by formula 1b, which comprises the steps according to Scheme 2:
1) preparing a compound of formula 5 by HX

[Scheme 2]

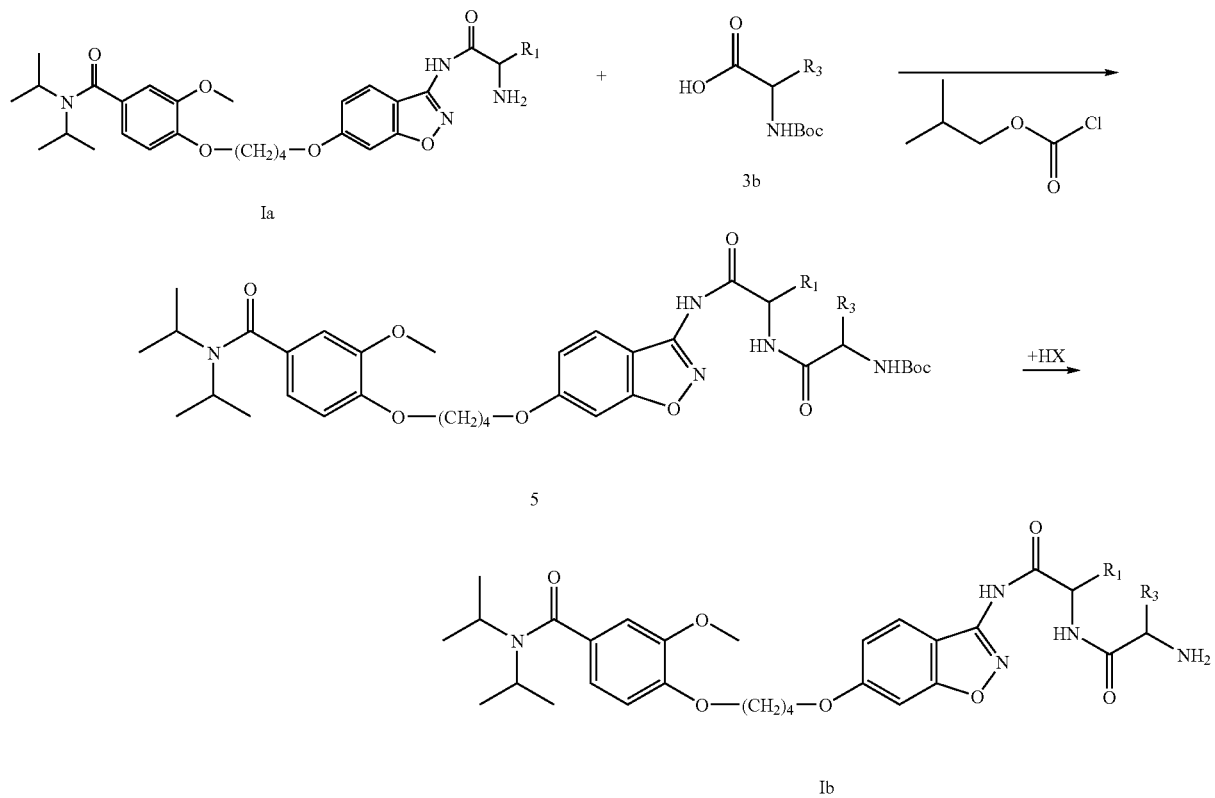

(wherein, $R_1$ is hydrogen, hydroxymethyl group, straight or branched alkyl group of $C_1$~$C_6$, benzyl group or 2-methylthioethyl group; $R_3$ is hydrogen, hydroxymethyl group, striaght or branched alkyl group of $C_1$~$C_6$, benzyl group or 2-methylthioethyl group; HX is hydrochloric acid, sulfuric acid, methane sulfonic acid or maleic acid.)

5. The method for preparing 3-amido-1,2-benzoisoxazole derivatives or pharmaceutically acceptable acidic additive salts according to claim 3 or 4, wherein the compound of formula 3a and 3b is selected from the group consisting of N-(t-butoxycarbonyl) glycine, N-(t-butoxycarbonyl)-L-alanine, N-(t-butoxycarbonyl)-L-phenylalanine, N-(t-butoxycarbonyl)-L-valine and N-(t-butoxycarbonyl)-L-methionine.

6. A pharmaceutical composition for an inhibitor or therapeutics for osteoporosis, comprising a 3-amido-1,2-benzoisoxazole derivative or a pharmaceutically acceptable acidic additive salt represented by the claim 1, as a medically effective ingredient.

* * * * *

UNITED STATES PATENT AND TRADEMARK OFFICE
CERTIFICATE OF CORRECTION

PATENT NO. : 7,291,638 B2
APPLICATION NO. : 10/493702
DATED : November 6, 2007
INVENTOR(S) : Lee et al.

It is certified that error appears in the above-identified patent and that said Letters Patent is hereby corrected as shown below:

Claim 1, Column 19, Lines 36-64, should read:

1.     3-amido-1,2-benzoisoxazole derivatives or pharmaceutically acceptable acidic additive salts, represented by the following formula 1:

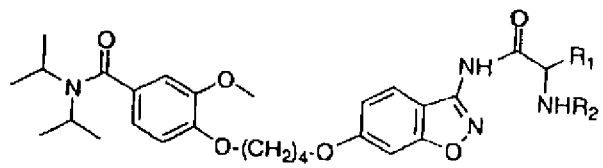

formula 1 wherein,
    $R_1$ is hydrogen, hydroxymethyl group, straight or branched alkyl group of $C_1 \sim C_6$, benzyl group or 2-methylthioethyl group;
    $R_2$ is hydrogen or $-COCH(NH_2)R_3$; and
    $R_3$ is hydrogen, hydroxymethyl group, straight or branched alkyl group of $C_1 \sim C_6$, benzyl group or 2-methylthioethyl group.

Claim 3, Column 20, Lines 1-61, should read as follows:

3.     A method for preparing 3-amido-1,2-benzoisoxazole derivatives or pharmaceutically acceptable acidic additive salts represented by formula 1a, which comprises the steps of:
    1)     preparing a compound of formula 4 by condensing a compound of formula 2 with a compound of formula 3a, and
    2)     preparing a compound of formula 1a by deprotecting a protecting group of the compound of formula 4 by HX, as follows:

UNITED STATES PATENT AND TRADEMARK OFFICE
CERTIFICATE OF CORRECTION

PATENT NO. : 7,291,638 B2
APPLICATION NO. : 10/493702
DATED : November 6, 2007
INVENTOR(S) : Lee et al.

It is certified that error appears in the above-identified patent and that said Letters Patent is hereby corrected as shown below:

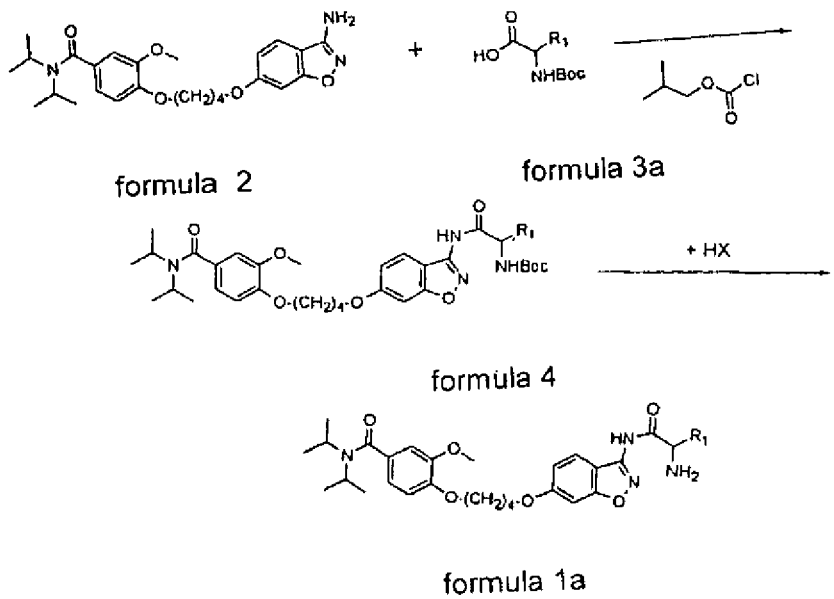

wherein,
$R_1$ is hydrogen, hydroxymethyl group, straight or branched alkyl group of $C_1 \sim C_6$, benzyl group or 2-methylthioethyl group; and
HX is hydrochloric acid, sulfuric acid, methane sulfonic acid or maleic acid.

Claim 4, Columns 20-21, Lines 62-67 and 1-43, should read:

4. A method for preparing 3-amido-1,2-benzoisoxazole derivatives or pharmaceutically acceptable acidic additive salts represented by formula 1b, which comprises the steps of:
 1) preparing a compound of formula 5 by condensing a compound of formula 3b with a compound of formula 1a prepared according to claim 7,
 2) preparing a compound of formula 1a by deprotecting a protecting group of the compound of formula 5 by HX, as follows:

UNITED STATES PATENT AND TRADEMARK OFFICE
CERTIFICATE OF CORRECTION

PATENT NO.        : 7,291,638 B2
APPLICATION NO. : 10/493702
DATED              : November 6, 2007
INVENTOR(S)     : Lee et al.

It is certified that error appears in the above-identified patent and that said Letters Patent is hereby corrected as shown below:

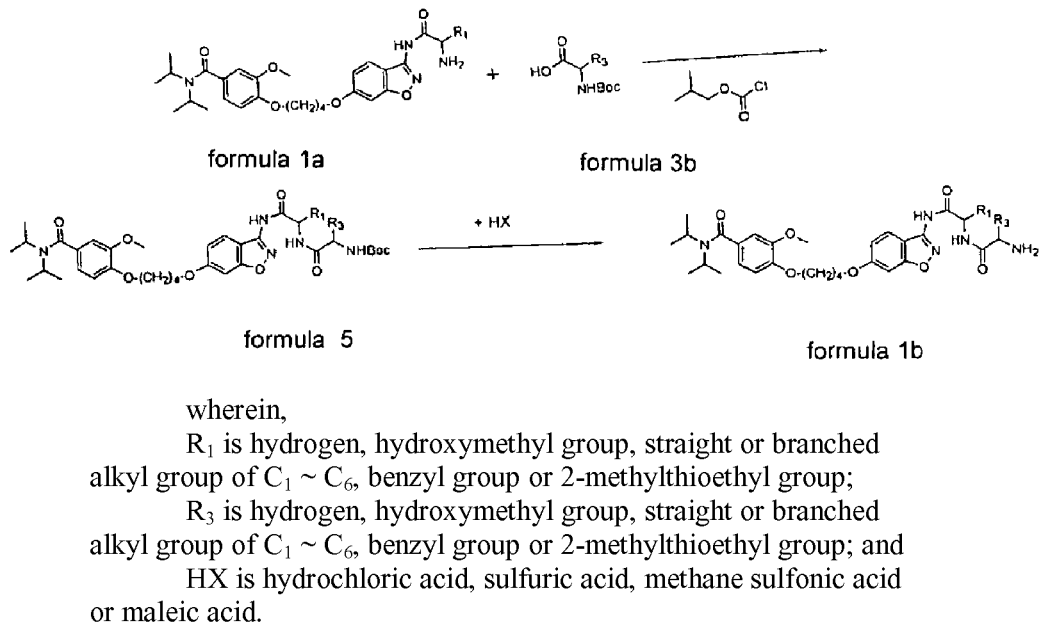

wherein,
$R_1$ is hydrogen, hydroxymethyl group, straight or branched alkyl group of $C_1 \sim C_6$, benzyl group or 2-methylthioethyl group;
$R_3$ is hydrogen, hydroxymethyl group, straight or branched alkyl group of $C_1 \sim C_6$, benzyl group or 2-methylthioethyl group; and
HX is hydrochloric acid, sulfuric acid, methane sulfonic acid or maleic acid.

UNITED STATES PATENT AND TRADEMARK OFFICE
CERTIFICATE OF CORRECTION

| | |
|---|---|
| PATENT NO. | : 7,291,638 B2 |
| APPLICATION NO. | : 10/493702 |
| DATED | : November 6, 2007 |
| INVENTOR(S) | : Lee et al. |

It is certified that error appears in the above-identified patent and that said Letters Patent is hereby corrected as shown below:

Claim 6, Column 22, Lines 41-45, should read:

6. A pharmaceutical composition for an inhibitor or therapeutics for osteoporosis, comprising a 3-amido-1,2-benzoisoxazole derivatives or pharmaceutically acceptable acidic additive salts according to claim 1, as a medically effective ingredient.

Signed and Sealed this

Seventh Day of July, 2009

JOHN DOLL
*Acting Director of the United States Patent and Trademark Office*